(12) United States Patent
Hanrahan

(10) Patent No.: US 8,800,574 B2
(45) Date of Patent: Aug. 12, 2014

(54) FLUFFY FLOSS KIT

(71) Applicant: Linda A. Hanrahan, South Easton, MA (US)

(72) Inventor: Linda A. Hanrahan, South Easton, MA (US)

( * ) Notice: Subject to any disclaimer, the term of this patent is extended or adjusted under 35 U.S.C. 154(b) by 0 days.

(21) Appl. No.: 13/692,558

(22) Filed: Dec. 3, 2012

(65) Prior Publication Data
US 2014/0150813 A1 Jun. 5, 2014

(51) Int. Cl.
*A61C 15/00* (2006.01)

(52) U.S. Cl.
USPC .......................................................... 132/325

(58) Field of Classification Search
CPC ...... A61B 17/24; A61C 15/04; A61C 15/042; A61C 15/043
USPC .................. 132/321, 324, 325, 329; 606/161; D28/65, 66
See application file for complete search history.

(56) References Cited

U.S. PATENT DOCUMENTS

| 1,069,874 | A |  | 8/1913 | Hanscom |
| 1,149,376 | A |  | 8/1915 | Leonard et al. |
| 1,285,988 | A |  | 11/1918 | Gudebrod |
| 1,637,153 | A |  | 7/1927 | Lawton |
| 1,893,524 | A |  | 1/1933 | Shanley |
| 2,667,443 | A |  | 1/1954 | Ashton |
| 2,700,636 | A |  | 1/1955 | Ashton |
| 3,699,979 | A |  | 10/1972 | Muhler et al. |
| 3,789,858 | A |  | 2/1974 | Pesce |
| 3,837,351 | A |  | 9/1974 | Thornton |
| 3,838,702 | A |  | 10/1974 | Standish et al. |
| 3,897,796 | A |  | 8/1975 | Erickson |
| 3,942,539 | A |  | 3/1976 | Corliss et al. |
| 4,008,727 | A |  | 2/1977 | Thornton |
| 4,265,258 | A |  | 5/1981 | Eaton, II |
| 4,582,059 | A |  | 4/1986 | Tiwari |
| 4,627,975 | A |  | 12/1986 | Lynch |
| 4,646,766 | A | * | 3/1987 | Stallard .......................... 132/325 |
| 4,922,936 | A |  | 5/1990 | Buzzi et al. |
| 5,063,948 | A | * | 11/1991 | Lloyd ............................ 132/321 |
| 5,209,251 | A |  | 5/1993 | Curtis et al. |
| 5,311,890 | A |  | 5/1994 | Thornton |
| 5,842,489 | A |  | 12/1998 | Suhonen et al. |
| 5,857,471 | A |  | 1/1999 | Harada |
| 6,016,816 | A |  | 1/2000 | Ariagno |
| 6,123,982 | A |  | 9/2000 | Fontana |
| D441,504 | S | * | 5/2001 | Stvartak et al. ................. D28/66 |
| 6,250,313 | B1 |  | 6/2001 | Rees |
| 6,428,554 | B1 |  | 8/2002 | Rosenblood et al. |
| 6,451,038 | B2 |  | 9/2002 | Rosenblood et al. |
| 6,575,176 | B1 |  | 6/2003 | Hill et al. |
| 6,591,844 | B2 |  | 7/2003 | Barlow et al. |
| 6,607,000 | B2 |  | 8/2003 | Marwah et al. |
| 6,644,323 | B1 |  | 11/2003 | Clark |
| 6,951,567 | B2 |  | 10/2005 | Levit |
| 7,152,611 | B2 |  | 12/2006 | Brown et al. |
| 8,132,579 | B1 | * | 3/2012 | Wien ............................. 132/321 |

(Continued)

*Primary Examiner* — Rachel Steitz
(74) *Attorney, Agent, or Firm* — John P. McGonagle

(57) ABSTRACT

A dental cleaning kit having a container internally holding a plurality of pieces or roll of dental floss is provided. The floss has a combination of tiny soft and stiff bristles formed thereto. The soft bristles are coated with a dried toothpaste, available in a variety of intense flavors. The kit container has a tongue scraper removably attached to the container's external surface. The floss is colored to correspond to a desired flavor. The container is colored to match the color of the floss contained therein.

1 Claim, 2 Drawing Sheets

(56) References Cited

U.S. PATENT DOCUMENTS

| | | | |
|---|---|---|---|
| 2001/0004701 A1* | 6/2001 | Rosenblood et al. | 606/161 |
| 2003/0154998 A1 | 8/2003 | Falleiros et al. | |
| 2006/0283477 A1* | 12/2006 | Oronsky et al. | 132/321 |
| 2009/0198262 A1 | 8/2009 | Rosenblood et al. | |
| 2010/0180912 A1 | 7/2010 | Ochs et al. | |
| 2010/0300481 A1 | 12/2010 | Lavrova | |

* cited by examiner

FLUFFY FLOSS KIT

BACKGROUND OF THE INVENTION

This invention relates to products used for the care of teeth, and in particular, to a kit containing dental floss for cleaning and brushing teeth, as well as a tongue scraper.

Residual food and plaque are primary causes of cavities and breakdowns of the supporting structure of the teeth and of periodontal diseases. There are many prophylactic dental products on the market today, which are useful for removing food and plaque from the interproximal spaces and proximal surfaces of the teeth. The most commonly used preventative product is the toothbrush. However, toothbrushes do not reach into the interproximal spaces and the proximal surfaces of the teeth. Toothpicks are also used for cleaning teeth and especially for removing food matter for the interproximal spaces between the teeth. However, toothpicks will often bruise the gums when used. Water picks also have been found effective for removing food particles from the interproximal spaces between teeth and thus prevent the buildup of plaque. However, water picks are not an effective means of removing plaque that has already formed. Dental flosses are also useful for cleaning teeth. However, waxed dental flosses are do not readily remove plaque. Unwaxed dental floss tends to tear and bruise gums.

Most people will use a combination of the above prophylactic dental products in their home to clean their teeth. When traveling or temporarily living elsewhere, e.g., vacation, temporary work assignment, overnight visits, etc., most people will find it impractical to take with them their dental cleaning products, e.g., water pick. When outside the routine of their home, many people will neglect to take full care of their teeth. What is needed is a dental cleaning kit, which is easily transportable, easy to use, and motivating to use.

SUMMARY OF THE INVENTION

The present invention overcomes the problems of the prior art by providing a dental cleaning kit. The present invention kit provides a container internally holding a plurality of pieces or roll of dental floss. The container is compact and easily carried in a purse or pocket. The floss has a combination of tiny bristles formed thereto, some of said bristles are soft and some are stiff. The soft bristles are coated with dried toothpaste, available in a variety of intense flavors. The embedded dried toothpaste is activated by water or saliva, creating a foamy cleanser. The floss actually cleans and brushes all surfaces of the teeth and massages the gum line, while removing plaque and food debris. The kit container may also have a tongue scraper removably attached to the container's external surface. The kit holds with one container all of the dental products needed to keep a person's teeth clean.

The floss may be wrapped around the tip of a finger and used to clean the front surfaces of a person's teeth like a toothbrush. The toothpaste used may be selected from a wide variety of flavors, e.g., peppermint, spearmint, wintergreen, cinnamon, tangerine/orange, melon, bubblegum, etc. It is contemplated that the floss would be colored to correspond to the flavor of the toothpaste used. The container would have a corresponding color.

These together with other objects of the invention, along with various features of novelty, which characterize the invention, are pointed out with particularity in the claims annexed hereto and forming a part of this disclosure. For a better understanding of the invention, its operating advantages and the specific objects attained by its uses, reference should be had to the accompanying drawings, claims and descriptive matter in which there is illustrated a preferred embodiment of the invention.

DETAILED DESCRIPTION OF INVENTION

Figure 1:
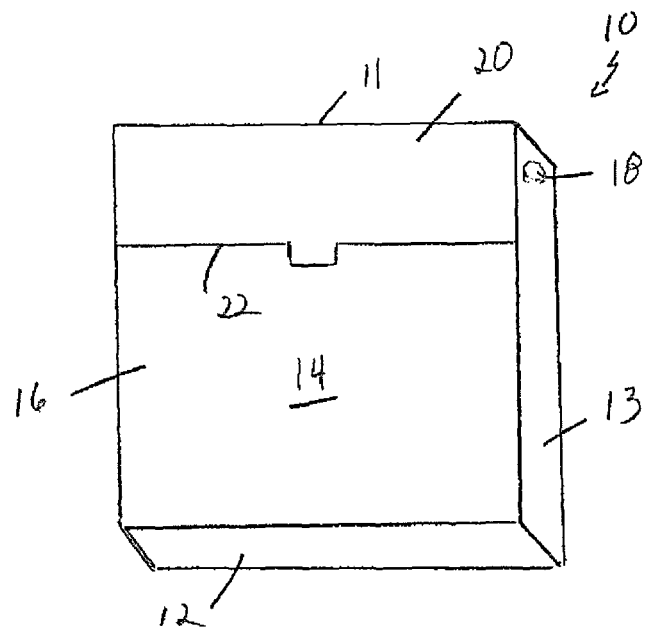
FIG. 1 is a front perspective view of a dental kit container.
Figures 2, 3:
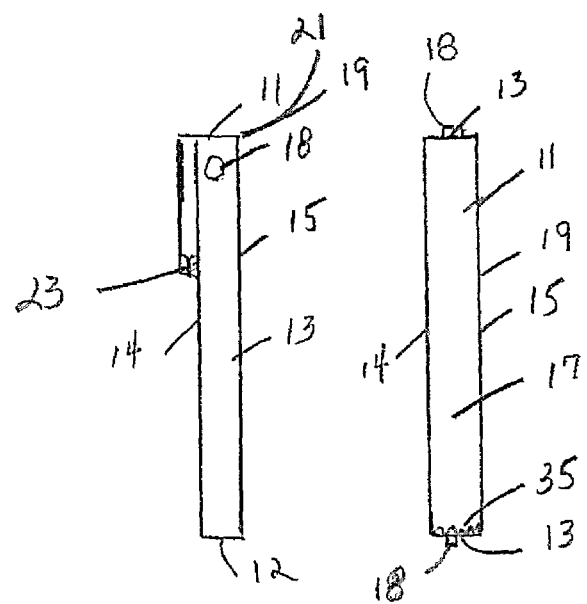
FIG. 2 is a side view of the dental kit container.
FIG. 3 is a top view of the dental kit container without a cover.
Figure 4:
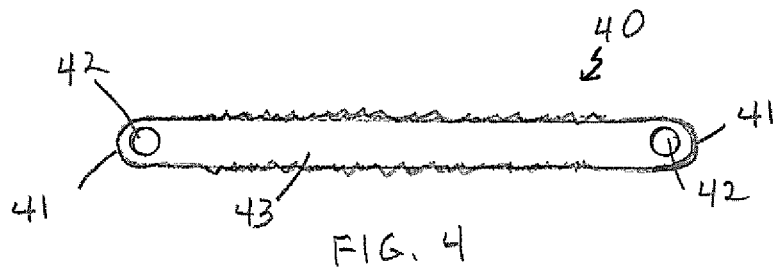
FIG. 4 is a representative view of a tongue scraper.
Figure 5:
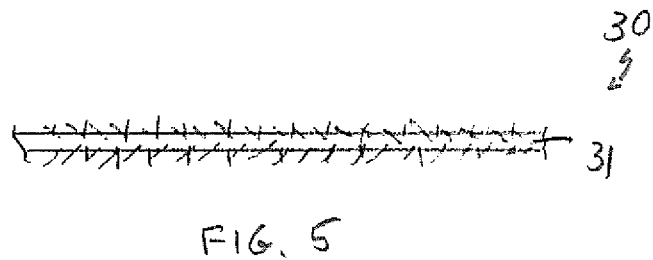
FIG. 5 is a diagrammed view of a section of invention dental floss.
Figure 6:
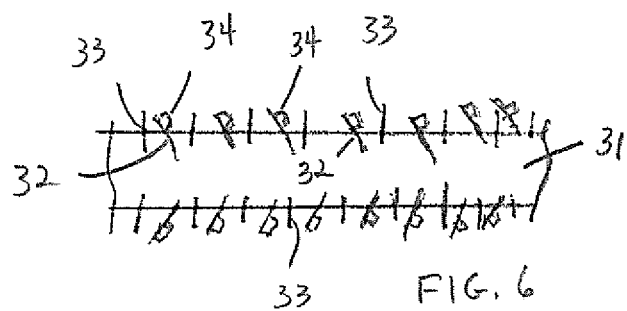
FIG. 6 is a diagrammed view of a blown up section of invention dental floss.
Figure 7:
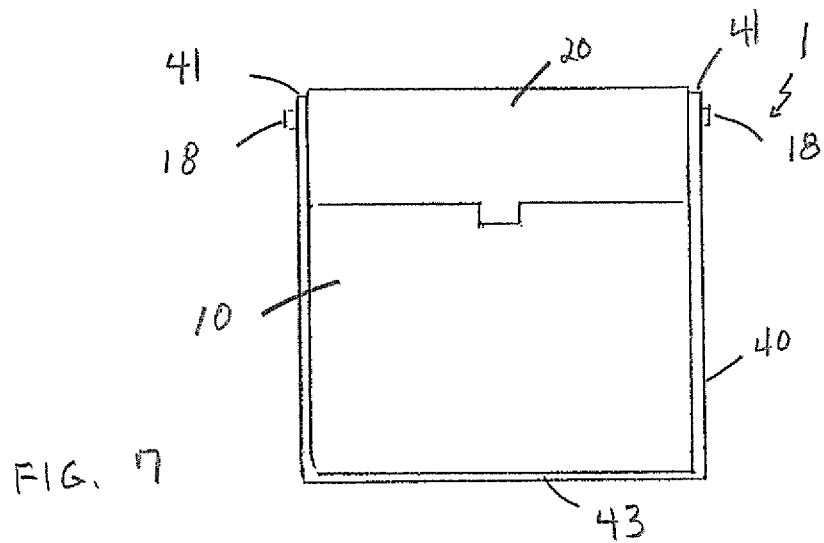
FIG. 7 is a front view of the invention kit.

Referring to the drawings in detail wherein like elements are indicated by like numerals, there is shown a dental cleaning kit 1 comprised of a container 10 internally holding a plurality of pieces or roll of dental floss 30. The container 10 has a tongue scraper 40 removably attached to the container's external surface.

The dental kit container 10 has a generally rectangular shape with a top 11, a bottom 12, opposite sides 13, a front 14, a rear 15, and an external surface 16, said top, bottom sides, front and rear defining a container interior 17. The container sides 13 each contain a nub 18 near to the container top 11. The container top 11 has a cover 20 pivotally attached to a junction 19 formed between the top 11 and rear 15. The cover 20 has an attachment end 21 joined to the junction 19. The cover 20 extends over the container top 11 to the container front 14 and has a forward end 22 removably attached to the container front 14 by means of a hook and pile fastener 23, such as sold under the VELCRO trademark.

The container interior 17 holds a plurality of pieces or roll of uniquely coated dental floss 30. Each floss strand 31 has a plurality of tiny soft bristles 32 incorporated thereto. Each floss strand 31 also has a plurality of tiny stiff bristles 33 incorporated thereto. The soft bristles 32 are coated with dried toothpaste 34. The toothpaste 34 is flavored. The embedded toothpaste 34 is activated by water or saliva. The container interior 17 may contain a stiff cutting piece 35 of metal or plastic at the container top 11 and one of the sides 13 to cut a desired length of floss 30. The soft bristles 32 act as a toothbrush with access to all areas about a tooth. The stiff bristles 33 dislodge dental debris and plaque about a tooth. A standard elongated tongue scraper 40 is also provided. The tongue scraper 40 has an elongated body 43 with two ends 41, each end having a finger hole 42 incorporated therein. The tongue scraper 40 is removably attached to the container 10 by placing the tongue finger holes 42 over the container side nubs 18. The tongue scraper body 43 snugly fits against the container sides 13 and bottom 12 until removed from the container 10.

It is contemplated that the floss 30 would be colored to correspond to a selected flavor. The container external surface 16 would have a color matching the color of the floss 30 held within the container interior 17.

It is understood that the above-described embodiment is merely illustrative of the application. Other embodiments may be readily devised by those skilled in the art, which will embody the principles of the invention and fall within the spirit and scope thereof.

I claim:

1. A dental cleaning kit, comprising:

a container having a generally rectangular shape with a top, a bottom, opposite sides, a front, a rear, and an external surface, said top, bottom sides, front and rear defining a container interior, each of said sides having a nub near to the container top;

a cover pivotally attached to a junction formed between the top and rear, said cover having an attachment end joined to the said junction, said cover extending over the container top to the container front, said cover having a forward end removably attached to the container front by means of a hook and pile fastener;

a stiff cutting piece at the container top and one of the sides to cut a desired length of dental floss; dental floss held within the container interior, said dental floss having a plurality of tiny bristles formed thereto, a portion of said bristles being soft and a portion of said bristles being stiff;

a coating of dried toothpaste on said soft bristles, said dried toothpaste adapted to being activated by saliva, said dried toothpaste having an intense flavor; and a tongue scraper removably attached to said container, wherein, the tongue scraper has an elongated body with two ends, each end having a finger hole incorporated therein, wherein the tongue scraper is removably attached to the container by placing the tongue finger holes over the container side nubs, wherein the tongue scraper body snugly fits against the container sides and bottom until removed from the container;

wherein, the dental floss is colored to correspond to a selected flavor and the container has said external surface colored to match the color of the dental floss held within the container interior.

* * * * *